(12) United States Patent
Schowanek et al.

(10) Patent No.: US 6,485,629 B1
(45) Date of Patent: Nov. 26, 2002

(54) PROCESS FOR SEPARATION OF HEAVY METALS FROM RESIDUES BY USE OF ETHYLENE-DIAMINE-DISUCCINIC ACID (EDDS) COMPLEXANT

(75) Inventors: Diederik Rudolf Schowanek, St. Amands (BE); Tom Cornelis Jan Feijtel, Hevillers (BE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/719,270

(22) PCT Filed: Jun. 11, 1999

(86) PCT No.: PCT/US99/13009

§ 371 (c)(1),
(2), (4) Date: Feb. 28, 2001

(87) PCT Pub. No.: WO99/66084

PCT Pub. Date: Dec. 23, 1999

(30) Foreign Application Priority Data

Jun. 19, 1998 (GB) .............................................. 9813234

(51) Int. Cl.⁷ ................................................. C22B 3/32
(52) U.S. Cl. ........................... 205/560; 423/43; 423/50; 423/55; 423/64; 423/65
(58) Field of Search ............................. 205/560; 423/43, 423/50, 55, 64, 65

(56) References Cited

U.S. PATENT DOCUMENTS 6,264,720 B1 * 7/2001 Schowanek et al.

FOREIGN PATENT DOCUMENTS

EP 0 853 986 7/1998

OTHER PUBLICATIONS

T–C. Chen, et al., "Selection and Test of Effective Chelators for Removal of Heavy Metals from Contaminated Soils," Can. J. Civ. Eng., vol. 22, (1995) pp 1185–1197.
P. M. Jardine, et al., "Fate and Transport of Ethylenediaminetetraacetate Chelated Contaminants in Subsurface Environments," Geoderma, Vol. 67, (1995) pp. 125–140.
S. B. Martin, Jr., et al., "Recycling EDTA After Heavy Metals Extraction," ChemTech, (Apr. 1996) pp 23–25.

* cited by examiner

*Primary Examiner*—Aruns S. Phasge
(74) *Attorney, Agent, or Firm*—Kevin L. Waugh

(57) ABSTRACT

A process for separating a first source of a heavy metal ion or mixtures of heavy metal ions, ($Me_1$), from a solution comprising a complex of said $Me_1$ and EDDS, ($Me_1$-EDDS), by displacement of said $Me_1$ with a second source of a heavy metal ion $Me_2$ by addition to the solution of a salt of said $Me_2$.

18 Claims, No Drawings

PROCESS FOR SEPARATION OF HEAVY METALS FROM RESIDUES BY USE OF ETHYLENE-DIAMINE-DISUCCINIC ACID (EDDS) COMPLEXANT

FIELD OF THE INVENTION

This invention relates to processes and materials for use therein for separating heavy metals from solutions or substrates, in particular from contaminated soil, sludges, sediments, and industrial residues. The invention also relates to processes and materials particularly suitable for metal recovery.

BACKGROUND OF THE INVENTION

If an aqueous solution containing a chelating or complexing agent is exposed to an environment (e.g., a waste material) containing a compound of one or more metals which can be chelated by that chelating agent, some or all of the metals will form a chelate with that chelating agent. A wide variety of chelating agents are known, for instance as reviewed by Chen et al at pages 1185 to 1197 of Can.J-.Civ.Eng.Vol 22, 1995. The equilibrium complexation constants for the various chelating agents with the various metals indicates the relative affinity and stability of any particular chelate and, when there is competition between metals, which metals will be chelated in preference to others. There are an extremely large number of chelating agents out of which a selection could be made, but in practice interest has concentrated on relatively few. For example citric acid and NTA are commonly used as hardness complexing agents and EDTA is usually the material of choice for chelating heavy metals.

Contamination of soils, sediments and municipal or industrial wastes by heavy metal pollutants is a major environmental problem. For instance there are areas of ground which are contaminated by industrial waste containing heavy metal such that there is a risk of the heavy metal getting into ground water, and there are large volumes of river and sea sediments which are contaminated with toxic heavy metals.

Some major engineering works have been conducted and are being proposed which are designed to treat the top soil or ground water, or the sediments or other municipal or industrial wastes in such a way as to reduce the heavy metal contamination, but they all suffer from an inherent problem. This problem arises from the fact that chelants (or other chemical reagents) that may be used for attempting to remove the heavy metal contamination from the soil tend to be relatively ineffective unless they form a very strong chelate with the relevant metal. If they do form a strong chelate, then the result of the process is merely to transfer the environmental problem from a contaminated substrate (which is often solid and reasonably concentrated) to a vast volume of a dilute solution of a stable chelate of the heavy metal.

For example, the article by Chen et al reports the screening of 190 chelating agents (including all those mentioned above) and examines in particular the performance of ADA (acetamido imino diacetic acid), SCMC (amino carboxy-alkyl thio proponoic acid) and PDA (pyridine dicarboxylic acid) but does not make any clear recommendations.

Other authors have concentrated on the use of EDTA and have noted its power for extracting heavy metals but have also noted the difficulty of recovering the heavy metal and recycling the EDTA (for instance Jardine et al in Geoderma 67 (1995) 125 to 140 and Martin et al Chem Tech April 1996 pages 23 to 25).

Other authors have concentrated on other ways of treating polluted sediments or ground waters from polluted soil and some of these processes have involved a biological treatment. However the same general problem remains, namely that either removal of the heavy metal is inefficient or the pollution problem is transferred from the soil or sediment in favour of a vast volume of dilute contaminated solution.

Further, the use of EDTA and other preferred chelating agents has the risk of the chelating agent subsequently causing further contamination of the environment, since they persist in the environment.

In co-pending European patent application 97870004.5. a process is described which enables the specific extraction of heavy metal from a water-immiscible substrate by contacting the substrate with [S,S]-EDDS, thereby forming an extract solution containing a complex of the heavy metal and [S,S] EDDS, whereafter the extract solution can be separated from the substrate and then in a separation step, the heavy metal can be separated from the complex and from the extract solution, in particularly by electro winning or precipitation.

It is preferred that the whole substrate/extract solution is treated under the same conditions and in the same separation process and under the same process conditions. However, in many instances, the water-immiscible substrate comprises various heavy metals and thus various complexes with EDDS are formed. The inventors have observed that the separation of mixtures of metal ions from EDDS complexes can be cumbersome.

They have now found an improved process to facilitate the removal of mixtures of heavy metal ions from EDDS complexes from a solution, whereby first the heavy metal ions in the EDDS complexes are displaced by one single heavy metal ion. The displaced heavy metal ions can then be recovered from the solution. In particular, they have found specific process conditions to be used to displace the heavy metal ions with one single heavy metal ion and specific conditions to separate or recover the displaced heavy metal ions from the solution.

Subsequently, the remaining EDDS complex comprising one single displacement heavy metal ion can be recovered by any of the separation methods described in co-pending European patent application 97870004.5, such as in particularly by electrolysis, electrowinning or precipitation.

Thus, the conditions of the process to separate or recover heavy metal ions can be optimised for one single complex-type and this thus allows more effective and costefficient heavy metal removal or separation from substrates or solutions.

SUMMARY OF THE INVENTION

The invention provides a process for separating a source of a first heavy metal ion or mixture of heavy metal ions, ($Me_1$), from a solution comprising a complex of said $Me_1$ and EDDS, ($Me_1$-EDDS), by displacement of said $Me_1$ with a source of a second heavy metal ion ($Me_2$) by addition to the solution of a salt of said $Me_2$.

In particular, the invention provides a process for separating a first source of a heavy metal ion or a mixture of heavy metal ions ($Me_1$) from a solution comprising a complex of said $Me_1$ and EDDS ($Me_1$-EDDS), comprising the steps of:

obtaining a solution having a pH 1 to 6, comprising the $Me_1$-EDDS;

b) addition to the solution of step a) of a second source of a heavy metal ion ($Me_2$) which is soluble in the solution having a pH 1 to 6, preferably in a molar stoichiometric excess to the EDDS which forms part of $Me_1$-EDDS, to produce a solution comprising a complex of $Me_2$ and EDDS ($Me_2$-EDDS);

c) addition of an alkaline material to the solution of step b) to increase the pH to at least 8.5, preferably at least 9, thereby obtaining a precipitate of $Me_1$, preferably in the form of a salt of $Me_1$;

d) optionally removing the precipitate of step c) from the solution.

The EDDS is preferably [S,S] EDDS.

DETAILED DESCRIPTION OF THE INVENTION

The process of the invention aims to facilitate the recovery of heavy metals from complexes of these metals with EDDS, in particular [S,S] EDDS. These complexes may be formed by processes of treating substrates containing heavy metal ions, such as contaminated soil, sludges, sediments, and industrial residues. Therefore, the process of the invention is preferably part of a process for separating heavy metals from substrates.

The invention provides a process for separating heavy metal from EDDS, ethylene diamine disuccinic acid or ethylene di-imine butane dioic acid. It can exist in various isomeric forms. The form which is preferably used in the invention is the [S,S] form. By "active" EDDS or [S,S]-EDDS, when used herein, is meant [S,S]-EDDS in the form of the ion, the free acid or the alkali metal salt or other chemical form such that it is capable of acting as a chelating agent for heavy metals.

The [S,S]-EDDS is a powerful complexing agent for heavy metals and is readily biodegradable. For instance it is rapidly and substantially completely degraded in a suitable environment within 28 days, and usually within 14 days or less in a batch test. The [S,R] and [R,R] isomers are not readily biodegradable according to EU and OECD regulations. Generally therefore at least 80% by weight and preferably at least 95% by weight of total EDDS is in the [S,S]-EDDS form. Preferably the proportion of [S,S] isomer is as high as is reasonably practicably, preferably as close to 100% as is conveniently attainable, or even 100%.

If any other complexing agents are used in the processes herein, it is preferred that they should be biodegradable with the result that the amount of non-biodegradable complexing agent used in the processes of the invention is kept to a minimum, and is preferably less than 50%, and most preferably less than 20% or 10% by weight based on total complexing agent and preferably is zero or as near zero as is conveniently possible.

As an essential step in the process of the invention, a first source of a heavy metal ion $Me_1$ is displaced by a second source of a heavy metal ion. By first source of a heavy metal ion, when used herein, is meant any compound or complex comprising any heavy metal ion, preferably a heavy metal salt or heavy metal ion, but in particularly a mixture of heavy metal ions or heavy metal salts. In particular a source of Ca, Al, Mg, Cd, Hg, Zn, Pb, Ni, Cr, Co or mixtures thereof. By second source of a heavy metal ($Me_2$), when used herein, is meant any compound or complex comprising heavy metal ion, preferably, heavy metal salt or heavy metal ion, whereby, when the first source of heavy metal ions only comprises one type of heavy metal ions, the second source of heavy metal ions should comprise heavy metal ions different to the first heavy metal. Preferably, the first source of heavy metal ions comprises a mixture of heavy metal ions, optionally including Cu, and the second source of heavy metal ions comprises Cu.

To ensure efficient displacement, the process of the invention is such that the $Me_2$ has a stronger affinity for the active EDDS than the $Me_1$. In a preferred step of the process of the invention, a specific heavy metal $Me_2$, in particular Cu, displaces $Me_1$ at a pH from 1 to 6 or even from 1 to 3. Preferably, the $Me_2$ should be soluble in a solution at the specific pH, between pH 1 to 6. Preferably, this step comprises addition of a Cu salt, in particularly $CuSO_4$, to a solution of pH 1 to 6, or even 1 to 3, or even 2 to 3.

The $Me_2$ is preferably used in a molar stoichiometric excess compared to the EDDS which is part of $Me_1$ EDDS, preferably such that $Me_2/Me_1$-EDDS is from 1.05, to 3, or even $Me_2/Me_1$ is 1.05 to 3.

Then, in a subsequent step of the process of the invention, the displaced $Me_1$ are separated from the solution comprising the complex of $Me_2$-EDDS. This can be achieved by any separation process, but preferably this comprises precipitation of a salt of $Me_1$, including hydroxide salts of $Me_1$. Thus, the $Me_2$ or the process conditions are preferably selected such that $Me_2$ does not precipitate in this step and the $Me_2$-EDDS remains in the solution.

The step preferably comprises addition of an alkaline material to the solution, to increase the pH to at least 8.5, preferably at least 9, preferably up to 10.5. The alkaline material preferably comprises a hydroxide salt, and may comprise a carbonate salt, a phosphate salt or mixtures thereof, preferably calcium, magnesium, potassium or more preferably sodium salts thereof The $Me_1$ preferably precipitates in the form of a hydroxide salt.

The precipitate can be removed from the solution by any conventional method, including filtration and centrifugation.

Then, the process preferably comprises a recovery step of recovery of the EDDS by separating the $Me_2$ from the complex. This may be done by any known method in the art. Preferred may be methods of formation of a salt of $Me_2$, preferably a sulphide salt, and precipitation of said salt; electrolysis or electrowinning.

It may be preferred that the separation of the $Me_2$ from the $Me_2$-EDDS complex and the solution is conducted by a process which comprises biodegrading the [S,S]-EDDS moieties of the complex and thereby releasing $Me_2$ from the EDDS, and separating the released heavy metal from the extract solution (usually by precipitation). Aerobic degradation may preferably be conducted in any suitable reactor such as in a mixed aerated tank at 7 to 40° C. which contains an aqueous suspension of flocculated bacteria and into which the solution is pumped (i.e., an activated sludge system), or by a trickling filter through a sand or stone bed with bacteria on the solid particles, or by a fluidised bed reactor. The resultant solution, containing dissolved second heavy metal compound, can then be passed through an ion exchanger to recover the second heavy metal or can be subjected to precipitation, for instance under reduction with hydrogen sulphide, to form the sulphide precipitate. In any of these processes, the second heavy metal can, alternatively, be recovered by electrolytic precipitation from the extract solution after biodegradation.

$Me_2$ may also be separated from the $Me_2$-EDDS complex by ion exchange, electrowinning or electrolysis, or other techniques but preferably it is separated by precipitation, optionally in addition to the biodegradation process described above.

The precipitation may follow as a result of the formation of any suitable insoluble compound of the heavy metal, but generally the most convenient heavy metal compound to be formed as precipitate is the metal sulphide. This is usually formed by bacterial reduction of elemental sulphur, sulphate or other oxidized sulphur sources.

Extraction Processes

The process of the invention is preferably part of an extraction process for separating a first source of heavy metal ions ($Me_1$) preferably comprising mixtures of heavy metal ions from a immiscible substrate. The extraction process preferably comprises the steps of extracting $Me_1$ from a substrate by contacting the substrate with an aqueous treatment solution containing active EDDS and thereby forming an extract solution comprising a complex of EDDS and $Me_1$, being $Me_1$-EDDS, and then separating the extract solution from the substrate, optionally lowering the pH of the extract solutions to pH, to 6, to obtain the solution of step a) of the process of the invention.

In such an extraction process processes, also other component may be used to facilitate the extraction, such as one or more materials selected from (1) microorganisms or enzymes for promoting release of heavy metal from the substrate, (2) biodegradable surfactant for promoting release of heavy metal from the substrate and/or emulsifying hydrophobic material from the substrate into the aqueous treatment solution, (3) biodegradable hardness chelating agent for preferentially chelating calcium and/or magnesium and/or ferrous metal from the substrate, (4) flotation, coagulation or flocculation agent, and (5) acid, base or buffer for altering or controlling the pH of the substrate to a working optimum range.

The substrate to be submitted to the extraction process is preferably water immiscible and insoluble in the sense that it is possible to extract the heavy metal from the substrate by contacting the substrate with the aqueous treatment solution whilst avoiding dissolution of most or all of the substrate into the treatment solution. Generally little or no dissolution of the substrate occurs into the treatment solution.

The substrate may be a water-immiscible liquid. For instance it may be oil contaminated with zinc or other heavy metal or a solid or semi-solid material, for instance as a slurry.

Preferred extraction processes whereby the process of the invention may be useful are described in co-pending European patent application 97870004.5.

What is claimed is:

1. A process for separating a first source of a heavy metal ion or a mixture of heavy metal ions ($Me_1$) from a solution comprising a complex of said $Me_1$ and EDDS ($Me_1$-EDDS), the steps of said process comprising:
   a) obtaining a solution having a pH 1 to 6, comprising said $Me_1$-EDDS;
   b) addition to said solution of step a) of a second source of a heavy metal ion ($Me_2$), which is soluble in said solution having a pH 1 to 6, to produce a solution comprising a complex of $Me_2$ and EDDS ($Me_2$-EDDS);
   c) addition of an alkaline material to said solution of step b) to increase the pH to at least 8.5 thereby obtaining a precipitate of $Me_1$; and
   d) optionally removing said precipitate of step c) from said solution.

2. A process according to claim 1 wherein said EDDS comprises at least 80% [S,S] EDDS.

3. A process according to claim 2 wherein said EDDS comprises at least 100% [S,S] EDDS.

4. A process according to claim 1 whereby in step b) $Me_2$ is $CuSO_4$ and $Me_2$-EDDS is Cu-EDDS.

5. A process according to claim 1 whereby in step a) the pH of said solution is from 1 to 3.

6. A process according to claim 1, whereby said alkaline material in step c) is selected from the group consisting of an alkali or alkaline earth hydroxide salt, a carbonate salt or phosphate salt, and mixtures thereof.

7. A process according to claim 6 whereby said solution of step a) is obtained by an extraction process for separating a source of a first heavy metal ion ($Me_1$) from a immiscible substrate comprising the steps of:
   a) extracting $Me_1$ from the substrate by contacting the substrate with an aqueous treatment solution containing active [S,S]-EDDS;
   b) forming an extract solution comprising a complex of [S,S]EDDS and $Me_1$, being $Me_1$-EDDS;
   c) separating the extract solution from the substrate; and
   d) optionally lowering the pH of the extract solution to a pH of 1 to 6.

8. A process according to claim 7 in which said substrate comprises an oil contaminated with a heavy metal.

9. A process according to claim 7 in which said substrate is a solid selected from the group consisting of industrially contaminated soil, river or harbor sediment, waste from a mineral recovery plant, cellulosic waste solids, industrial waste sludge solids, municipal sewage sludge solids, and mixtures thereof.

10. A process according to claim 1, further comprising said removal step comprising:
   a) separating said $Me_2$-EDDS from said solution;
   b) separating said $Me_2$ from said EDDS; and
   c) removal of said $Me_2$ by a process selected from the group consisting of precipitation, electrowinning, electrolysis; and mixtures thereof.

11. A process according to claim 10 wherein said EDDS comprises at least 80%.

12. A process according to claim 11, wherein said EDDS comprises at least 100% [S,S] EDDS.

13. A process according to claim 11, wherein said process of step (b) further comprises a process of biodegradation of said [S,S] EDDS moiety.

14. A process according to claim 10, wherein said separation of said $Me_2$ from said EDDS is by the formation of a salt of $Me_2$.

15. A process according to claim 14, wherein said salt is a sulphide salt.

16. A process according to claim 1, wherein said second source of a heavy metal ion is provided in a molar stoichiometric excess to said EDDS which forms part of said $Me_1$-EDDS.

17. A process according to claim 1, wherein the addition of said alkaline material to said solution of step b) increases the pH to at least 9.

18. A process according to claim 1, wherein said precipitate of $Me_1$ is in the form of a salt of $Me_1$.

* * * * *